United States Patent
Rudolph et al.

(10) Patent No.: US 9,528,927 B2
(45) Date of Patent: Dec. 27, 2016

(54) WEATHERING TESTING HAVING A PLURALITY OF RADIATION SOURCES WHICH ARE INDEPENDENTLY OPERABLE OF ONE ANOTHER

(71) Applicant: ATLAS MATERIAL TESTING TECHNOLOGY GMBH, Linsengericht-Altenhasslau (DE)

(72) Inventors: Bernd Rudolph, Alzenau (DE); Peter March, Frankfurt am Main (DE)

(73) Assignee: ATLAS MATERIAL TESTING TECHNOLOGY GMBH, Linsengericht-Altenhasslau (DE)

(*) Notice: Subject to any disclaimer, the term of this patent is extended or adjusted under 35 U.S.C. 154(b) by 219 days.

(21) Appl. No.: 14/477,105

(22) Filed: Sep. 4, 2014

(65) Prior Publication Data

US 2015/0068328 A1 Mar. 12, 2015

(30) Foreign Application Priority Data

Sep. 6, 2013 (EP) .................................... 13183376

(51) Int. Cl.
*G01N 17/00* (2006.01)
(52) U.S. Cl.
CPC .......... *G01N 17/004* (2013.01); *G01N 17/002* (2013.01)
(58) Field of Classification Search
CPC .... G01N 17/004; G01N 17/00; G01N 17/002; G01N 2021/3133; G01N 21/31; G01N 21/55; G01N 2201/1241
See application file for complete search history.

(56) References Cited

U.S. PATENT DOCUMENTS

| | | | | |
|---|---|---|---|---|
| 2,804,770 A | * | 9/1957 | Meyer .................. | G01N 17/004 73/150 R |
| 3,224,266 A | * | 12/1965 | Klippert ................. | G01N 17/00 73/150 R |
| 3,426,590 A | * | 2/1969 | Nagaichi .................. | G01J 3/14 73/150 R |
| 3,488,681 A | * | 1/1970 | Masakatsu ............. | G01N 17/00 374/57 |
| 3,576,125 A | * | 4/1971 | Kockott ............... | G01N 17/004 374/57 |
| 3,886,791 A | * | 6/1975 | Grossman .............. | G01N 17/00 73/150 R |

(Continued)

FOREIGN PATENT DOCUMENTS

| | | |
|---|---|---|
| DE | 3221392 | 12/1983 |
| DE | G 91 00 816.6 | 4/1991 |

(Continued)

OTHER PUBLICATIONS

Extended European Search Report issued Oct. 16, 2013, in corresponding European Patent Application No. 13183376.6.

*Primary Examiner* — David A Rogers (57) ABSTRACT

The apparatus for artificially weathering or testing the lightfastness of samples has a weathering chamber, in which at least one sample can be arranged, and a plurality of radiation sources, which are arranged in the weathering chamber and which are operable independently of one another, wherein the apparatus is configured in such a way that the at least one sample is movable on a closed path around the plurality of radiation sources.

4 Claims, 5 Drawing Sheets

(56) References Cited

U.S. PATENT DOCUMENTS

| | | | | |
|---|---|---|---|---|
| 3,983,742 A * | 10/1976 | Suga | ................... | G01N 17/004 374/57 |
| 4,391,522 A * | 7/1983 | Schmid | ................... | G01J 3/02 356/326 |
| 4,627,287 A * | 12/1986 | Suga | ................... | G01N 17/004 73/159 |
| 4,704,903 A * | 11/1987 | Suga | ................... | G01N 17/00 73/159 |
| 4,760,748 A * | 8/1988 | Katayanagi | ................... | G01N 17/004 374/57 |
| 4,817,447 A * | 4/1989 | Kashima | ................... | G01N 17/004 374/57 |
| 4,831,564 A * | 5/1989 | Suga | ................... | G07C 3/00 324/414 |
| 4,843,893 A * | 7/1989 | Huber | ................... | G01N 17/004 374/138 |
| 4,874,952 A * | 10/1989 | Arnaud | ................... | G01N 17/004 250/455.11 |
| 4,957,011 A * | 9/1990 | Huber | ................... | G01N 17/00 236/DIG. 9 |
| 5,136,886 A | 8/1992 | Neigoff et al. | | |
| 5,138,892 A * | 8/1992 | Suga | ................... | G01N 17/004 374/57 |
| 5,226,318 A * | 7/1993 | Huber | ................... | G01N 17/004 73/159 |
| 5,660,794 A * | 8/1997 | Gilbreath, Jr. | ................... | G01N 17/004 250/492.1 |
| 5,854,433 A * | 12/1998 | Patel | ................... | G01N 17/004 73/159 |
| 5,898,816 A * | 4/1999 | Heeger | ................... | G01N 17/004 392/408 |
| 6,466,313 B1 * | 10/2002 | Bernatek | ................... | G01N 17/004 250/372 |
| 7,154,378 B1 * | 12/2006 | Ertas | ................... | A61B 1/00059 340/309.16 |
| 7,348,581 B2 * | 3/2008 | March | ................... | G01N 17/004 250/504 R |
| 7,353,722 B2 * | 4/2008 | Schonlein | ................... | G01N 17/00 250/492.1 |
| 7,759,873 B2 * | 7/2010 | Mastenbroek | ................... | H05B 41/36 250/493.1 |
| 9,063,050 B2 * | 6/2015 | Suga | ................... | G01N 17/004 |
| 2002/0139928 A1 * | 10/2002 | Rathod | ................... | A45C 7/0095 250/252.1 |
| 2003/0060682 A1 * | 3/2003 | Handa | ................... | A61B 1/0669 600/178 |
| 2004/0113102 A1 * | 6/2004 | Wedekamp | ................... | A61L 2/10 250/504 R |
| 2004/0233520 A1 * | 11/2004 | Ketola | ................... | G01N 17/002 359/361 |
| 2005/0087768 A1 * | 4/2005 | March | ................... | G01N 17/004 257/200 |
| 2005/0167580 A1 * | 8/2005 | Scott | ................... | G01N 17/002 250/252.1 |
| 2006/0254372 A1 * | 11/2006 | Scott | ................... | G01N 17/002 73/865.6 |
| 2007/0177144 A1 * | 8/2007 | Hasegawa | ................... | G01J 3/02 356/328 |
| 2008/0185539 A1 * | 8/2008 | Mastenbroek | ................... | H05B 41/36 250/503.1 |
| 2010/0000344 A1 | 1/2010 | Kaji et al. | | |
| 2011/0079071 A1 * | 4/2011 | Schultz | ................... | G01N 17/004 73/1.01 |

FOREIGN PATENT DOCUMENTS

| | | |
|---|---|---|
| EP | 0 487 202 A1 | 5/1992 |
| EP | 1 528 388 A1 | 5/2005 |
| JP | 57211528 A * | 12/1982 |
| JP | 62090523 A * | 4/1987 |
| JP | 63081246 A * | 4/1988 |

* cited by examiner

Fig. 5B

WEATHERING TESTING HAVING A PLURALITY OF RADIATION SOURCES WHICH ARE INDEPENDENTLY OPERABLE OF ONE ANOTHER

CROSS-REFERENCE TO RELATED APPLICATION

This application claims the foreign priority benefit of European Patent Application No. 13183376.6, filed on Sep. 6, 2013, with the European Patent Office, the disclosure of which is incorporated herein by reference.

BACKGROUND

Field

The present invention relates to an apparatus for artificially weathering or testing the lightfastness of samples and to a method for artificially weathering or testing the lightfastness of samples.

Description of Related Art

In apparatuses for artificial weathering, an assessment of the weathering-induced aging response of a sample, in particular a flat material sample, is performed, wherein the sample is subjected to artificial weathering. For this purpose, such apparatuses generally have a weathering chamber, in which holding means for holding samples to be weathered and a radiation source for applying radiation, in particular UV radiation, to the samples are arranged.

In such apparatuses for artificially weathering or testing the lightfastness of material samples, the intention is usually to estimate the life of materials which are continuously subjected to natural weather conditions during use and are therefore impaired under climatic influences such as sunlight, solar heat, moisture or the like. In order to obtain good simulation of the natural weathering conditions, it is advantageous if the spectral energy distribution of the light generated in the apparatus at least corresponds to that of the natural solar radiation, for which reason xenon gas discharge lamps are used as radiation source in such devices. In addition, accelerated aging testing of the materials is achieved substantially by virtue of very intensified radiation, in comparison with natural conditions, of the samples, as a result of which the aging of the samples is accelerated. Therefore, after a comparatively short period of time, it is possible to draw a conclusion on the long-term aging response of a material sample.

A large proportion of the material samples investigated in artificial weathering devices consists of polymeric materials. In the case of such materials, the weathering-induced impairment is substantially caused by the UV component of solar radiation. The photochemical primary processes occurring in the process, i.e. the absorption of photons and the generation of excited states or free radicals, are independent of temperature. Conversely, the subsequent reaction steps with the polymers or additives can be temperature-dependent, with the result that the observed aging of the materials is likewise temperature-dependent.

In the previously known weathering test devices, usually a xenon gas discharge lamp is used as radiation source. Such a xenon gas discharge lamp can be used, as is known, to simulate the solar spectrum quite well, but a conventional xenon lamp only has a nominal life of approximately 1500 hours at maximum irradiance. This means that the lamp can be operated at the maximum irradiance for this time period.

Furthermore, in principle metal halide lamps or fluorescent lamps can also be used as radiation sources for weathering devices. These lamps generally have a longer life than xenon lamps, but tend to be inferior to xenon lamps in terms of their spectral quality.

SUMMARY

It is therefore the object of the present invention to specify an apparatus for artificially weathering or testing the lightfastness of samples and a method for artificially weathering or testing the lightfastness of samples with which an effective service life of the radiation sources used in the apparatus can be extended.

This object is achieved by the features of the independent patent claims. Advantageous developments and configurations are the subject matter of dependent claims.

An apparatus for artificial weathering or testing of light fastness can be configured in such a way that a plurality of samples to be investigated which are fastened on a holding frame are moved on a closed path around a radiation source frame by virtue of the holding frame performing a rotation about a central axis. The radiation source, in particular a xenon gas discharge lamp, can be arranged on or along this axis of rotation. For the case where only one xenon gas discharge lamp is provided, once it has been switched on for the first time, said xenon gas discharge lamp can be operated, for example, constantly at a relatively high radiation intensity of 60 W/cm$^2$, for which a life of 1500 hours, for example, can be guaranteed by the manufacturer, wherein this value for the radiation intensity is an exemplary value and is generally dependent on the lamp type, the filtering and the distance to the lamp. Such a high output power represents a relatively high level of loading for the xenon lamp, however, which results in correspondingly rapid aging. In addition, it is known that the field strength occurring in the vicinity of the cathode, the so-called cathode drop, increases as the electrical input power increases during operation of the xenon lamp. A high cathode drop is, however, one cause of a short life of the xenon lamp. On the other hand, precisely in the case of weathering devices, a high radiated power of the xenon lamp tends to be desirable since this is a precondition for efficient accelerated aging testing of the samples in the weathering device.

A concept on which the present invention is based therefore consists in influencing the aging response of the radiation sources. This can be achieved by virtue of the fact that not only one radiation source but two or more radiation sources are arranged within a weathering chamber of the apparatus for artificial weathering or testing of lightfastness. These plurality of radiation sources are advantageously operable or drivable independently of one another, with the result that it is possible to provide a total light output power which is as high as desired for efficient accelerated aging testing of the samples, but at the same time to ensure that the radiation sources, for example, are not operated at a very high power or, for example, are only operated at a high power for time periods of limited duration and therefore their aging process can be slowed down.

The present invention therefore relates to an apparatus for artificially weathering or testing the lightfastness of samples comprising a weathering chamber, in which at least one sample can be arranged, a plurality of radiation sources, which are arranged in the weathering chamber and which are operable independently of one another, wherein the apparatus is configured in such a way that the at least one sample is movable on a closed path around the plurality of radiation sources.

In accordance with one embodiment of the apparatus, two or three radiation sources are arranged in the weathering chamber. However, it is also possible, if appropriate, for more than three radiation sources to be arranged in the weathering chamber.

In accordance with one embodiment of the apparatus, the radiation sources are formed by xenon gas discharge lamps.

However, other types of radiation sources are also possible, such as, for example, metal halide lamps or fluorescent lamps.

In accordance with one embodiment of the apparatus, a holding frame is arranged in the weathering chamber, and the samples to be investigated can be fastened in a suitable manner on said holding frame. The holding frame can be set in intrinsic rotary motion, wherein in particular the axis of rotation or axis of symmetry of the rotary motion coincides substantially with the position of the radiation sources, wherein, in the case of radiation sources arranged next to one another, the axis of rotation passes through the geometric center between the radiation sources, for example.

In accordance with one embodiment of the apparatus, the radiation sources are operable in temporal succession and/or at least partially simultaneously. For the case where the radiation sources are formed by gas discharge lamps, the gas discharge lamps can have suitable ballasts. In this case, the ballasts are actuable independently of one another. In particular, a control device which has a plurality of outputs can be provided in order to connect said outputs to a plurality of ballasts of gas discharge lamps or generally to a plurality of radiation sources.

In accordance with one embodiment of the apparatus, said apparatus furthermore has a sensor for sensing the radiated power of the radiation sources. An output of the sensor can be connected to an input of a control device for transferring a signal representing the measured radiated power. The sensor can in particular be arranged in such a way that it is moved along as a sample and therefore "sees" precisely the same radiation as the samples on its path around the radiation sources. In this case, the sensor can be arranged on the same plane as the samples and in particular can be held within a holding device such as a holding frame ("rack") in essentially the same way as the samples. The sensor can in particular also be designed in such a way that it generates a cosine-corrected measurement signal and transfers this to the control unit. This means that the sensor is designed to determine the dependence of the measured radiation intensity on the angle between the impinging radiation and the surface normal of the sensor or a pixel of the sensor and to determine a measurement signal which takes into consideration or corrects this dependence.

However, it is also possible for a plurality of sensors to be arranged, wherein each sensor can be assigned to one of the radiation sources and can be arranged in the weathering chamber in such a way that it measures the radiated power of the radiation source assigned thereto and an output of each sensor is connected to an input of the control device for transferring a signal representing the measured radiated power. In this case, too, the sensors can be designed in such a way that they can emit cosine-corrected measurement signals.

The control device can be configured in such a way that an optimum operating mode is determined on the basis of a combined radiated power of the radiation sources which is desired by a user, in which optimum operating mode the radiation sources are subjected to as low loads as possible. For this purpose, an expert system for determining the optimum operating mode can be provided within the control device.

In accordance with one embodiment of the apparatus, each radiation source is provided with a storage device, in which data relating to the radiation source can be or are stored. The storage device can be designed, for example, in such a way that it can be used for authorizing and/or identifying the radiation source. For example, information can be stored on said storage device which said storage device identifies as originating from a specific manufacturer and/or which it uniquely identifies. The storage device can in particular be provided as part of an RFID chip or RFID tag. Furthermore, data such as the operating hours provided by each radiation source and/or a residual life of the radiation source can be determinable and storable on the storage device. For this purpose, the storage device can be connected to the radiation source in such a way that it is readable by the control device when inserted into the weathering chamber and connected to the connection contacts. In the control device, the operating hours provided by the respective radiation source can then be counted and subsequently either the operating hours provided and/or the residual life of the control device can be stored on the storage device. The operating hours provided and/or the residual life can be used by the control device likewise for determining the optimum operating mode. The control device can also be designed in such a way that it only brings a radiation source into operation when an initial authorization and/or identification on the basis of the data obtained from the storage device has yielded a positive result according to preset criteria.

A method for artificially weathering or testing the lightfastness of samples has the following steps:
   a. providing a weathering chamber, which has a plurality of radiation sources which are operable independently of one another and a holding device for samples, by means of which the samples can be guided on a closed path around the radiation sources;
   b. arranging at least one sample in the holding device; and
   c. exposing the sample to radiation from the radiation sources, wherein the radiation sources are operated temporally successively and/or at least partially simultaneously.

In accordance with one embodiment of the method, two radiation sources can be provided, and the total expected service life of the two radiation sources can be divided into three phases, wherein, in a first phase, only a first radiation source is operated, in a second phase only a second radiation source is operated, and in a third phase both radiation sources are operated simultaneously.

In accordance with one embodiment of the method, two radiation sources can be provided and, during the entire expected service life of the two radiation sources, said radiation sources can be operated simultaneously.

In accordance with one embodiment of the method, the radiated power or radiation intensity of the radiation emitted by the radiation sources can be measured continuously and the measured radiation values can be compared with an expected setpoint profile and, in the event of discrepancies between the measured time profile of the measured radiated power and the setpoint profile, the electric power supplied to the radiation source can be increased or decreased correspondingly.

BRIEF DESCRIPTION OF DRAWINGS

The invention will be explained in greater detail below with reference to exemplary embodiments in conjunction with the figures in the drawing, in which.

DESCRIPTION OF EMBODIMENTS

Figure 1A:
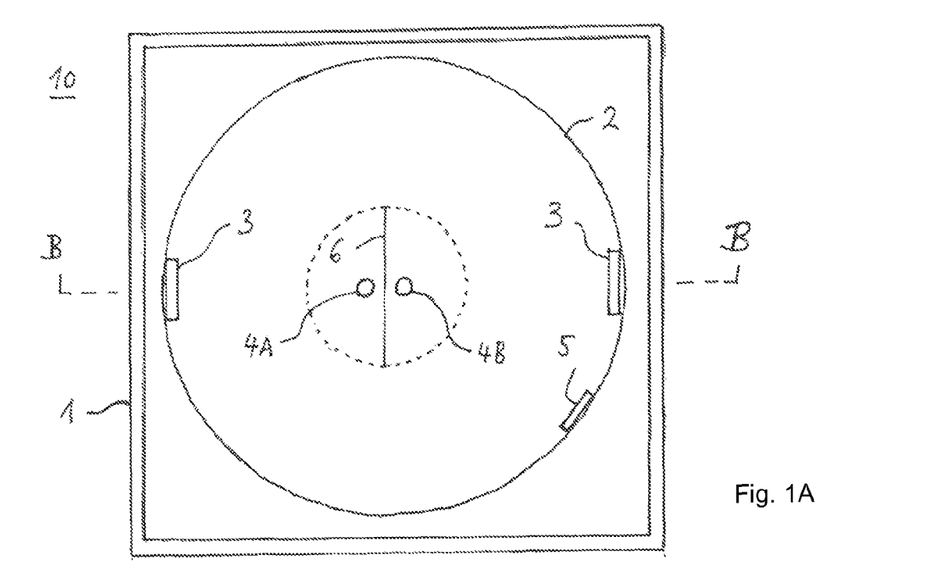
FIGS. 1A and 1B show a cross section (A) and a longitudinal section (B) through an embodiment of an apparatus for artificial weathering or testing of lightfastness comprising two radiation sources and a concomitantly guided sensor.
Figure 1B:
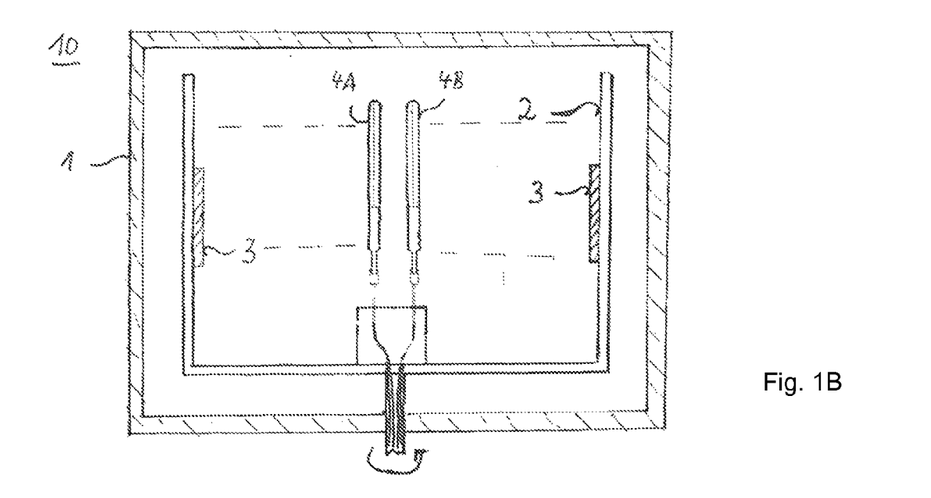

FIGS. 1A and 1B show an embodiment of an apparatus 10 for artificially weathering or testing lightfastness of samples in a cross section (A) and a longitudinal section (B), schematically.

The apparatus 10 comprises a weathering chamber 1, within which artificial weathering or testing of the lightfastness of samples can be performed. An annularly closed holding frame 2 is mounted rotatably in the weathering chamber 1 and has, on its inner side, suitably shaped holding elements (not shown), by means of which samples 3 or workpieces, for example rectangular varnished samples of standardized size, can be held. The holding frame 2 is in particular circular in a lateral cross section, with the result that the samples 3 are guided on a closed circular path on rotation of the holding frame 2. Two radiation sources 4A and 4B are arranged within the holding frame 2 and substantially concentrically therewith and can be formed by, for example, xenon gas discharge lamps. As illustrated, the two radiation sources 4A and 4B can be formed by elongate or longitudinal radiation bodies, in particular glass bulbs, which are aligned parallel to one another. The entire arrangement can be rotationally symmetrical such that an axis of rotation of the rotary movement of the holding frame 2 coincides with a mid-axis or axis of symmetry of the two radiation sources 4A and 4B. Provision may be made for it to be possible for a plurality of samples 3 to be fastened on the holding frame 2, in particular on holding elements provided for this purpose and arranged in the circumferential direction of the holding frame 2. Moreover, the samples 3 can also be fastened on the holding frame 2 one above the other in a plurality of planes. The radiation sources 4A and 4B can be operable or actuable independently of one another, as will be mentioned in more detail further below.

Furthermore, a radiation sensor 5 can be arranged in the weathering chamber 1 and detects the radiated power of the radiation emitted by the radiation sources 4A and 4B. The radiation sensor 5 can be fastened, in the same way as the samples 3, on the holding frame 2 and revolve with said samples around the radiation arrangement comprising the two radiation sources 4A, B, i.e. can be in the form of a concurrent radiation sensor 5. The output signal of the radiation sensor 5 can be supplied to an external control device, as will be described in more detail below. The radiation sensor 5 can be designed in such a way that it outputs an instantaneous radiated power detected by said radiation sensor as a corresponding electrical measurement signal. Provision can furthermore be made for an absorber plate 6 to be arranged between the radiation sources 4A and 4B so that the radiation sensor 5 detects in each case only the radiation emitted by one of the radiation sources 4A, B in any conceivable position on its orbit. The radiation sensor 5 can, as illustrated, be arranged offset with respect to the samples 3 in the circumferential direction of the holding device 2. It could likewise readily be arranged offset with respect to the samples 3 in the vertical direction even without any circumferential offset or be arranged offset with respect to the samples 3 both in the vertical and circumferential directions.

The weathering chamber 1 can, in a manner known per se, have further devices for artificial weathering, such as, for example, moisture generators or the like, but no further details of these are provided below. It is also possible, for example, for an air flow to be introduced into the weathering chamber 1, which air flow sweeps past the samples 3 and/or the radiation sources 4A and 4B in the vertical direction.

Figure 2:
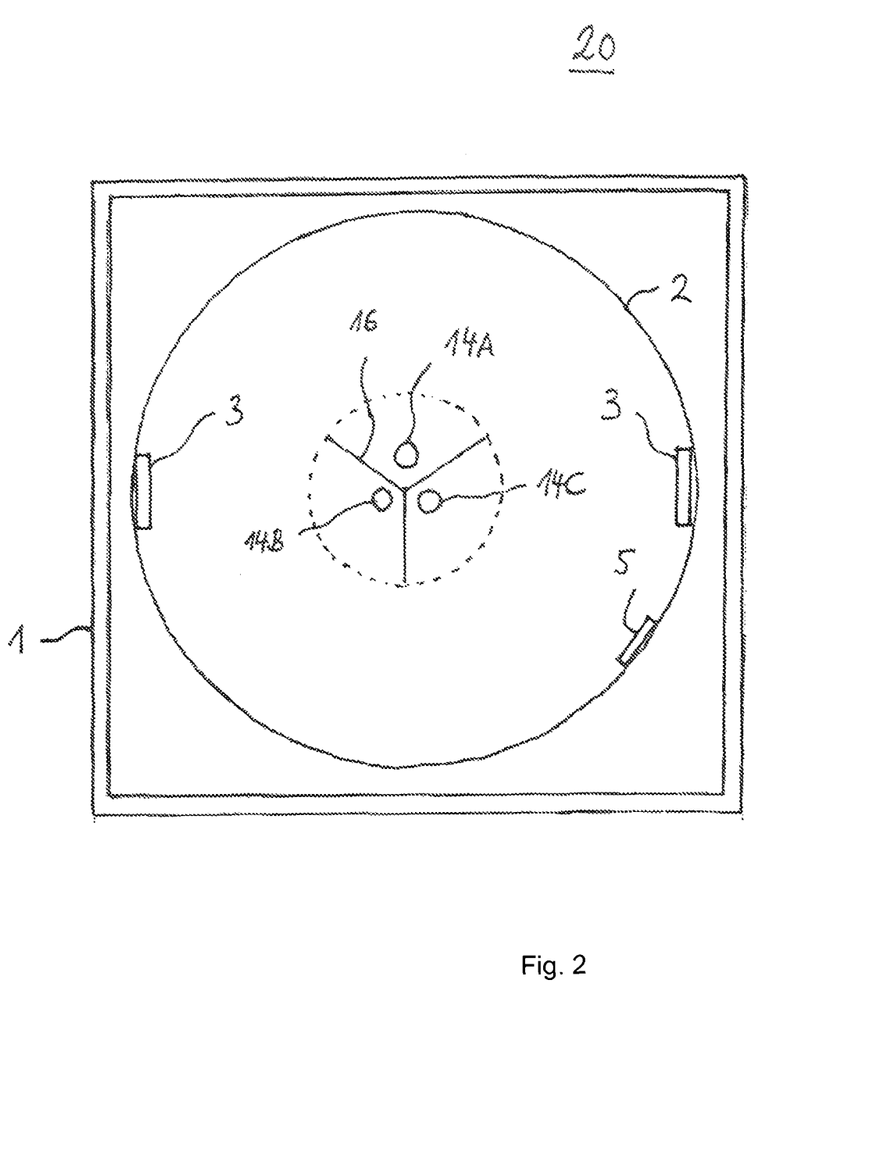
FIG. 2 shows a cross section through an embodiment of an apparatus for artificial weathering or testing of lightfastness comprising three radiation sources and one concomitantly guided sensor.

The apparatus can have two or three radiation sources and possibly also more than three radiation sources. FIG. 2 illustrates an exemplary embodiment which shows an apparatus 20 in a cross section. FIG. 2 shows an apparatus 20 comprising three radiation sources 14A, 14B and 14C. The radiation sources 14A, 14B and 14C can also be operable and actuable independently of one another. Furthermore, they can be arranged in cylindrically symmetrical fashion around a mid-axis or axis of symmetry, which can at the same time be the axis of rotation of the holding frame 2. It should also be mentioned that the radiation sources 14A, B, C do not necessarily need to be arranged in cylindrically symmetrical fashion with respect to the axis of rotation of the holding frame 2 since, as a result of the rotary movement of the samples 3 during the analysis, these samples 3 are in any case subjected to the radiation from the radiation sources on average uniformly. The apparatus 20 in FIG. 2 has a radiation sensor 5, which is fastened, in the same way as the samples 3, on the holding frame 2 and revolves with the samples 3 around the radiation arrangement comprising the plurality of radiation sources 14A, B, C. The radiation sensor 5 can be designed in such a way that it outputs an instantaneous radiated power detected by said radiation sensor as a corresponding electrical measurement signal. In addition, provision can be made for absorber plates 16 to be arranged between the radiation sources 14A, 14B and 14C, with the result that the radiation sensor 5 in each case only detects the radiation emitted by one of the radiation sources 14A, B, C in any conceivable position on its orbit. The radiation sensor 5 can, as illustrated, be arranged offset with respect to the samples 3 in the circumferential direction of the holding device 2. It could likewise readily be arranged offset with respect to the samples 3 in the vertical direction without any circumferential offset or be arranged offset both in the vertical and in the circumferential directions with respect to the samples 3. In the embodiments shown in FIGS. 1 and 2, it may also be possible for two or more revolving radiation sensors to be provided.

Figure 3:
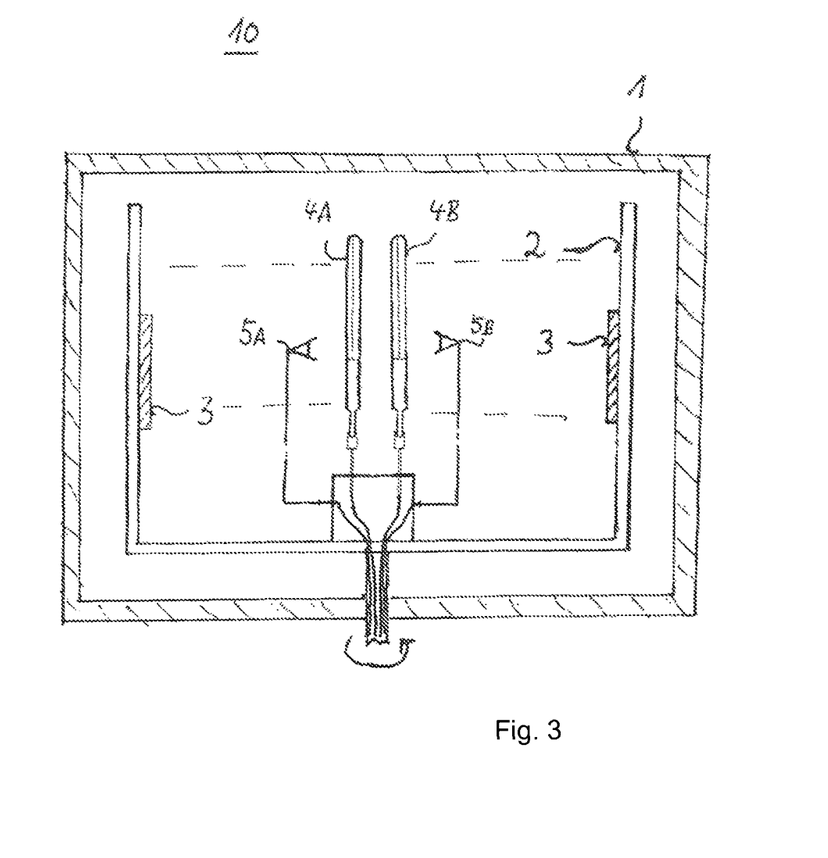
FIG. 3 shows a longitudinal section through an embodiment of an apparatus for artificial weathering or testing of lightfastness comprising two radiation sources and two stationary sensors.

FIG. 3 schematically illustrates a further embodiment in a longitudinal section. It is substantially equivalent to the embodiment shown in FIGS. 1A, B apart from the fact that no concurrent radiation sensor is arranged, but rather stationary radiation sensors 5A, 5B are arranged, which detect the radiated power of the radiation emitted by the radiation sources 4A and 4B. The radiation sensors 5A, 5B can in particular be arranged in such a way that each of the radiation sensors 5A and 5B in each case only detect the radiated power emitted by one of the two radiation sources 4A and 4B. The output signals of the radiation sensors 5A and 5B can be supplied to an external control device, as will be described in more detail below.

Figure 4:
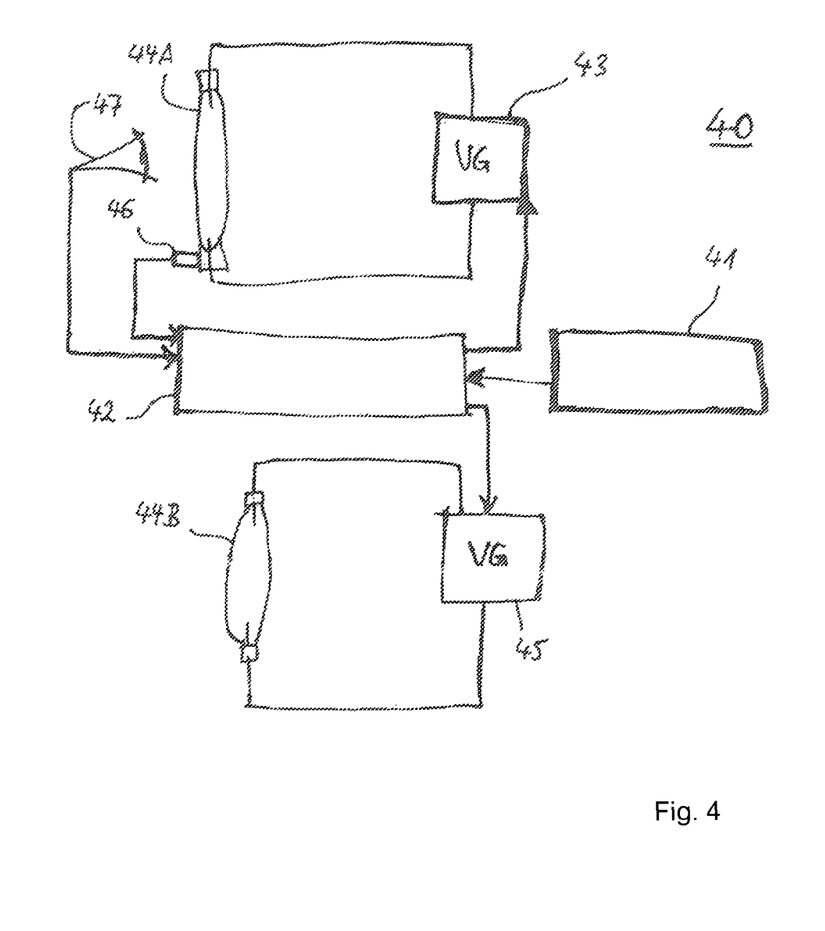
FIG. 4 shows a schematic block circuit diagram of a circuit for actuating two radiation sources of an apparatus for artificial weathering or testing of lightfastness of samples.

FIG. 4 shows a block circuit diagram illustrating the actuation of the radiation sources of an apparatus for artificial weathering or testing of lightfastness. The circuit arrangement 40 serves the purpose of actuating two different radiation sources 44A and 44B independently of one another. The radiation sources in FIG. 4 can be formed by gas discharge lamps, which can each be connected to ballasts. A first radiation source 44A can be connected with its connection contacts to a first ballast 43, and a second radiation source 44B can be connected with its connection contacts to a second ballast 45. The two radiation sources 44A and 44B can be provided by gas discharge lamps, in particular xenon gas discharge lamps. The circuit arrangement 40 can furthermore have a user interface 41, by means of which a user can initiate a test run for testing of weathering or testing of lightfastness of samples by inputting a certain operating mode or certain desired parameters. A desired parameter can be, for example, a radiated power to be emitted by each of the two radiation sources 44A and 44B or else a total radiated power to be achieved additively by both radiation sources. The user interface 41 can be connected on the output side to a control device 42, such as a microcontroller or microprocessor. The control device 42 can have two different outputs, which can be connected to the two ballasts 43 and 45. The control device 42 is therefore capable of actuating the ballasts 43 and 45 and therefore ultimately the radiation sources 44A and 44B differently, in particular on the basis of an input by a user at the user interface 41. It is possible, for example, for a specific program mode with a specific, preset designation (for example XenoLogic) to be provided which is selectable by the user and which the control device 42 instructs to operate the radiation sources 44A and 44B taking into consideration a total radiated power additionally also input by the user in such a way that a maximum service life results for both radiation sources. This can mean, for example, that when a test run is started, only one of the two radiation sources is operated for a preset period of time and then the second radiation source is connected thereto. However, should a total radiation intensity of 60 W/cm$^2$ be desired by a user, for example (depending on the lamp type and at a specific distance from the lamp), provision can also be made for both radiation sources to be operated at a radiation intensity of 30 W/cm$^2$ from the beginning.

In addition to these presets, further information can also be supplied to the control device 42 by the user interface 41, which information can be used by said control device for controlling the radiation sources 44A and 44B. Thus, for example, as shown in the previous exemplary embodiments, a radiation sensor 47 can be provided which detects the radiation emitted in each case by the radiation sources 44A, B and transfers a measurement signal representing the detected radiated power to the control device 42. The radiation sensor 47 can be in the form of a revolving radiation sensor. In the illustration in FIG. 4, the radiation sensor 47 is instantaneously oriented to the radiation source 44A and therefore instantaneously measures the emitted radiated power thereof. If, for example, the performance of the radiation source 44A should now decline and the radiation sensor 47 should detect this correspondingly and signal this to the control device 42, the control device 42 can provide for a correspondingly higher electric power to be provided to the ballast 43. In the same way, the radiation emitted by the second radiation source 44B can also be detected by the radiation sensor 47 and a measurement signal representing the radiated power provided to the control device 42.

Provision can also be made for one or both of the radiation sources 44A and 44B to be provided with a storage device 46, in particular an electronic circuit such an RFID chip, on which a code or other data of various types, such as, for example, the operating hours provided by the radiation source, can be stored. The RFID chip 46 can be connected, in particular non-detachably, to the respective radiation source, and in particular provision can be made for it not to be possible for it to be disconnected from the radiation source by a user without any damage being caused. During operation of the radiation source, the control device 42 can measure how long and at what output radiated power the radiation source has already been operated and the result can be stored on the electronic circuit. Each time the radiation source is brought into operation again, first the electronic circuit 46 can be read and the result can be supplied to the control device 42, which takes into consideration this result for its calculation of the optimum operating mode of said radiation source and the other radiation sources for a subsequent test run. Furthermore, provision can also be made for an expert system to be stored in the control device 42, to which expert system all of the data, in particular sensor data, remaining life data, desired total radiated power, etc., can be supplied, and which thereupon decides the way in which the radiation sources should be operated with the aim of achieving as long a service life as possible.

Figure 5A:
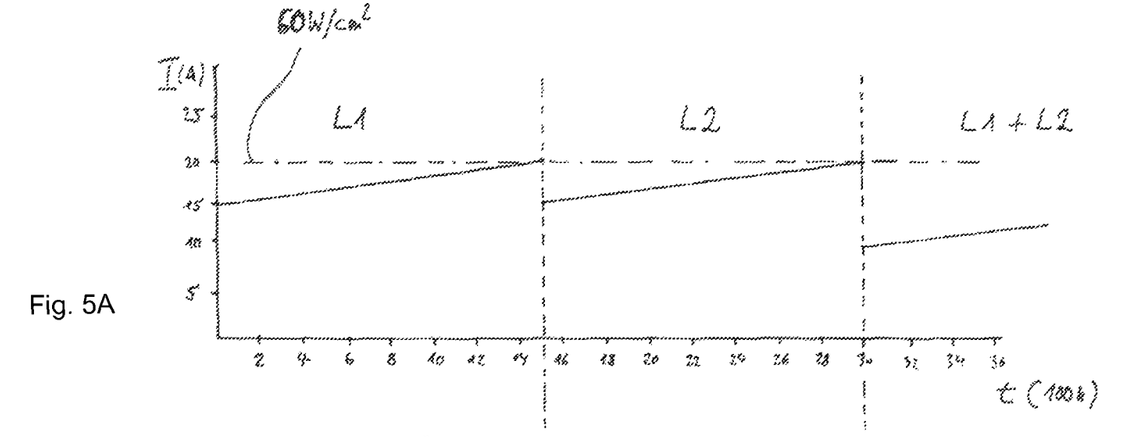
FIGS. 5A and 5B show timing diagrams illustrating two different operating modes when using two radiation sources.

FIG. 5A shows a timing diagram illustrating a possible mode of operation of two radiation sources of a weathering device. It is assumed that two radiation sources L1 and L2 are provided and that a desired total radiation intensity of 60 W/cm$^2$ has been input by a user, which is indicated in the diagram by the dash-dotted line. The mode of operation substantially consists in operating only the first radiation source L1 during a first phase lasting 1500 hours, operating only the second radiation source L2 during a second phase, likewise lasting 1500 hours, and operating both radiation sources L1 and L2 during a third phase. In each of the three phases, the radiation sources are intended to be provided with an electric power such that a total radiation intensity of 60 W/cm$^2$ results. For the first phase, this means that the first radiation source L1 is provided at the start time with a current of 15 A, which is increased continuously and linearly to a value of 20 A over the duration of the first phase of 1500 hours. This increase is necessary since, owing to the continuous decrease in power of the radiation source, the radiation intensity of 60 W/cm$^2$ can only be kept constant in this way. After 1500 operating hours, the nominal and guaranteed life of the first radiation source L1 is reached. The first radiation source L1 is then disconnected and at the same time the second radiation source L2 is switched on and is operated in the same way as the first radiation source L1 during the first phase. Once a further 1500 hours of the second radiation source L2 have elapsed, both radiation sources L1 and L2 are operated at 10 A, wherein this value is also increased linearly over time, as a result of which the output radiation intensity of 60 W/cm$^2$ remains constant. This can then be operated until one or both of the radiation sources has reached the actual end of its life. Since both radiation sources are only operated up to their nominal life of 1500 hours and then, in the third phase, only operated further to a considerably lower level, it is possible to achieve an extension of the service life.

Figure 5B:
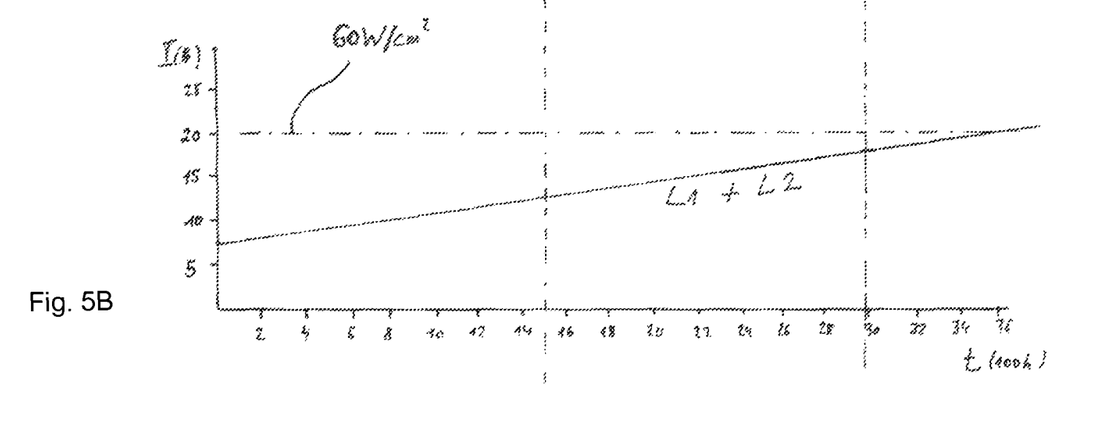

FIG. 5B shows a further timing diagram illustrating a further mode of operation. In this mode of operation, too, it is assumed that a total radiated power of 60 W/cm² has been set by a user at the user interface. However, this mode of operation envisages operating both radiation sources L1 and L2 over the entire time period. This means that, at the start time, both radiation sources are provided with an input current of 7.5 A, and this current is increased continuously and linearly in order to be able to constantly achieve the radiated power of 60 W/cm². Since both radiation sources are therefore only loaded to a relatively low level, it is possible to achieve an extended service life.

In the case of both timing diagrams, it is assumed that the increase in the electric power is based on empirical values and is fixed in advance in the controller. However, the procedure may also be such that the radiated power of each of the radiation sources L1 and L2 is measured by a radiation sensor, as described in the exemplary embodiments in FIGS. 1 to 4, and supplied to the control device 42, which correspondingly regulates the supply of electric power to the respective radiation source or the ballast. Furthermore, it is possible to take into consideration the fact that one or both of the radiation sources L1 and L2 has already been activated previously and therefore a specific number of operating hours have already been provided, which are stored on its storage device, in particular the RFID chip. This is read by the control device 42, which reacts correspondingly and subjects one or both radiation sources to correspondingly lower loads.

Although specific embodiments have been illustrated and described in this description, a person skilled in the art will recognize that the specific embodiments shown and described can be replaced with a multiplicity of alternative and/or equivalent implementations without departing from the scope of protection of the present invention. This application is intended to disclose any modifications or changes to the specific embodiments set forth in this document. It is therefore provided that this invention is only limited by the claims and equivalents thereof.

What is claimed is:

1. An apparatus for artificially weathering or testing the lightfastness of samples, comprising:
    a weathering chamber, configured to house at least one sample and a plurality of radiation sources, which are operable independently of one another, the radiation sources being operable in temporal succession and/or at least partially simultaneously, and each of the radiation sources being provided with an electronic circuit, used for identification of the radiation source, wherein the operating hours provided and/or a residual life of the radiation source is determinable and storable on the electronic circuit;
    a user interface by means of which a user can input a desired total radiated power to be achieved additively by the plurality of radiation sources;
    a control device, which is configured to generate control signals for actuating the radiation sources, the control device being connected with the user interface; and
    a plurality of sensors, wherein each of the sensors is assigned to one of the radiation sources and is arranged in such a way that it measures the radiated power of the assigned radiation source, and an output of each of the sensors is connected to an input of the control device for transferring a power signal representing the measured radiated power, wherein
    the control device is configured to read the electronic circuit of each one of the radiation sources, and
    the control device is configured to determine the electrical power to be supplied to the radiation sources in dependence on the power signals delivered by the sensors and in dependence on the values of the operating hours provided and/or the residual life stored in the electrical circuits, so that the total radiated power corresponds to the desired total radiated power input by the user, and to incorporate the determined electrical power into the control signals for actuating the radiation sources.

2. The apparatus as claimed in claim 1, in which
    the radiation sources include two or three radiation sources, and
    the weathering chamber is configured to house the two or three radiation sources.

3. The apparatus as claimed in claim 1, in which
    the radiation sources are formed by xenon gas discharge lamps.

4. A method for artificially weathering or testing the lightfastness of samples, comprising:
    providing a weathering chamber, which has two radiation sources which are operable independently of one another and a holding device for samples, by means of which the samples can be guided on a closed path around the radiation sources;
    arranging at least one sample in the holding device; and
    exposing the sample to radiation from the radiation sources, wherein
    the radiation sources are operated temporally successively and/or at least partially simultaneously, and
    a total expected service life of the two radiation sources is divided into three phases, wherein, in a first phase, only a first radiation source is operated, in a second phase, only a second radiation source is operated, and in a third phase, both radiation sources are operated simultaneously.

* * * * *